United States Patent
Yamada et al.

(10) Patent No.: US 9,375,013 B2
(45) Date of Patent: Jun. 28, 2016

(54) HERBICIDAL COMPOSITION

(71) Applicant: ISHIHARA SANGYO KAISHA, LTD., Osaka (JP)

(72) Inventors: Ryu Yamada, Shiga (JP); Hiroyuki Okamoto, Shiga (JP); Takashi Terada, Shiga (JP)

(73) Assignee: ISHIHARA SANGYO KAISHA, LTD., Osaka (JP)

( * ) Notice: Subject to any disclaimer, the term of this patent is extended or adjusted under 35 U.S.C. 154(b) by 0 days.

(21) Appl. No.: 14/768,318

(22) PCT Filed: Feb. 19, 2014

(86) PCT No.: PCT/JP2014/053949
§ 371 (c)(1),
(2) Date: Aug. 17, 2015

(87) PCT Pub. No.: WO2014/129512
PCT Pub. Date: Aug. 28, 2014

(65) Prior Publication Data
US 2016/0000085 A1    Jan. 7, 2016

(30) Foreign Application Priority Data
Feb. 22, 2013   (JP) ................... 2013-033556

(51) Int. Cl.
| | |
|---|---|
| *A01N 47/36* | (2006.01) |
| *A01N 43/50* | (2006.01) |
| *A01N 43/66* | (2006.01) |
| *A01N 51/00* | (2006.01) |

(52) U.S. Cl.
CPC ............. *A01N 47/36* (2013.01); *A01N 43/50* (2013.01); *A01N 43/66* (2013.01); *A01N 51/00* (2013.01)

(58) Field of Classification Search
CPC ........ A01N 47/36; A01N 43/50; A01N 43/66
See application file for complete search history.

(56) References Cited

U.S. PATENT DOCUMENTS

| | | | |
|---|---|---|---|
| 7,659,229 B2 | 2/2010 | Volgas et al. | |
| 2011/0166023 A1 | 7/2011 | Nettleton-Hammond et al. | |
| 2011/0190136 A1* | 8/2011 | Hufnagl ................ | A01N 43/90 504/136 |
| 2014/0106971 A1* | 4/2014 | Kikugawa ............. | A01N 47/36 504/136 |

FOREIGN PATENT DOCUMENTS

| | | |
|---|---|---|
| JP | 2012-153643 | 8/2012 |
| JP | 2012-158566 | 8/2012 |
| WO | 2008/142391 | 11/2008 |
| WO | 2009/054823 | 4/2009 |
| WO | 2015/078243 | 6/2015 |

OTHER PUBLICATIONS

R.H. Wells et al., "Effects of Imazapic and Flazasulfuron on Dallisgrass in Bermuda-grass Turf", 2009 Proceedings, Southern Weed Science Society, vol. 62, pp. 88.
International Third Party Observation in respect to International Application No. PCT/JP2014/053949, dated Sep. 12, 2014.
International Search Report in respect to International Application No. PCT/JP2014/053949, dated May 27, 2014.
International Preliminary Report on Patentability in respect to International Application No. PCT/JP2014/053949, dated Sep. 3, 2015.
S.R. Colby, "Calculating Synergistic and Antagonistic Responses of Herbicide Combinations", Weeds, pp. 20-22, (1967).

\* cited by examiner

*Primary Examiner* — John Pak
(74) *Attorney, Agent, or Firm* — Greenblum & Bernstein, P.L.C.

(57) ABSTRACT

At present, many herbicidal compositions have been developed and used, but they are not necessarily sufficient to control undesired plants such as weeds to be controlled in some cases, and a herbicidal composition having high activity has been desired.
A herbicidal composition comprising flazasulfuron or its salt, and at least one herbicidal compound selected from the group consisting of imazapic, hexazinone, mesotrione and their salts, and a method for controlling undesired plants using it.

17 Claims, No Drawings

HERBICIDAL COMPOSITION

TECHNICAL FIELD

The present invention relates to a herbicidal composition and a method for controlling undesired plants.

BACKGROUND ART

Patent Document 1 discloses a herbicidal composition comprising at least one acetolactate synthase inhibitor, at least one 4-hydroxyphenyl pyruvate dioxygenase-inhibitor and at least one saturated or unsaturated fatty acid.

Patent Document 2 discloses a composition comprising at least one sulfonylurea herbicide, diuron and hexazinone.

However, Patent Documents 1 and 2 failed to specifically disclose a remarkable synergistic effect by combination of flazasulfuron or its salt and at least one herbicidal compound selected from the group consisting of imazapic, hexazinone, mesotrione and their salts.

PRIOR ART DOCUMENTS

Patent Documents

Patent Document 1: WO2008/142391
Patent Document 2: WO2009/054823

DISCLOSURE OF INVENTION

Technical Problem

At present, many herbicidal compositions have been developed and used, but they are not necessarily sufficient to control undesired plants such as weeds to be controlled in some cases, and a herbicidal composition having high activity has been desired.

Solution to Problem

The present inventors have conducted extensive studies and as a result, found that a herbicidal composition having high activity can be obtained by combination of specific compounds, and accomplished the present invention.

That is, the present invention provides the following (1) to (4).

(1) A herbicidal composition comprising as active ingredients (A) flazasulfuron or its salt (hereinafter referred to as compound A) and (B) at least one herbicidal compound selected from the group consisting of imazapic, hexazinone, mesotrione and their salts (hereinafter referred to as compound B).

(2) The composition according to (1), wherein the mixing ratio of compound A to compound B is from 1:0.2 to 1:50 by the weight ratio.

(3) A method for controlling undesired plants or inhibiting their growth, which comprises applying a herbicidally effective amount of compound A and a herbicidally effective amount of compound B to the undesired plants or to a place where they grow.

(4) The method according to (3), wherein compound A is applied in an amount of from 10 to 100 g/ha, and compound B is applied in an amount of from 20 to 500 g/ha.

Advantageous Effects of Invention

According to the present invention, a herbicidal composition having high activity can be obtained.

When the herbicidal activity in a case where two active ingredients are combined, is larger than the simple sum of the respective herbicidal activities of the two active ingredients (the expected activity), it is called a synergistic effect. The activity expected by the combination of two active ingredients can be calculated as follows (Colby S. R., "Weed", vol. 15, p. 20-22, 1967).

$$E=(\alpha+\beta)-(\alpha\beta)/100$$

where $\alpha$: growth inhibition rate when treated with x (g/ha) of herbicide X, $\beta$: growth inhibition rate when treated with y (g/ha) of herbicide Y, E: growth inhibition rate expected when treated with x (g/ha) of herbicide X and y (g/ha) of herbicide Y.

That is, when the actual growth inhibition rate (measured value) is larger than the growth inhibition rate by the above calculation (calculated value), the activity by the combination can be regarded as showing a synergistic effect. The herbicidal composition of the present invention shows a synergistic effect when calculated by the above formula.

DESCRIPTION OF EMBODIMENTS

Compound A and compound B sometimes form salts or have isomers, and they are included in the present invention so long as they are agriculturally acceptable.

The mixing ratio of compound A to compound B cannot generally be defined, as it varies depending upon various conditions such as the type of the formulation, the weather conditions, and the type and the growth stage of the undesired plants, and is, for example, from 1:0.2 to 1:50, preferably from 1:0.8 to 1:40, further preferably from 1:1 to 1:30 by the weight ratio.

The herbicidally effective amounts of compounds A and B cannot generally be defined, as they vary depending upon various conditions such as the mixing ratio of compound A to B, the type of the formulation, the weather conditions, and the type and the growth stage of the undesired plants. However, for example, compound A is applied in an amount of from 10 to 100 g/ha, preferably from 10 to 50 g/ha, and compound B is applied in an amount of from 20 to 500 g/ha, preferably from 40 to 400 g/ha, further preferably from 50 to 300 g/ha.

The herbicidal composition of the present invention may be applied to undesired plants or may be applied to a place where they grow. Further, it may be applied at any time either before or after the emergence of the undesired plants. Further, the herbicidal composition of the present invention may take various application forms such as soil application, foliar application, irrigation application, and submerged application, and it can be applied to agricultural fields such as upland fields, orchards and paddy fields, and non-cropland such as ridges of fields, fallow fields, play grounds, golf courses, vacant lands, forests, factory sites, railway sides and roadsides.

The herbicidal composition of the present invention can control a wide range of undesired plants such as annual weeds and perennial weeds. The undesired plants to be controlled by the herbicidal composition of the present invention may, for example, be specifically cyperaceae such as green *kyllinga* (*Kyllinga brevifolia* Rottb. var. *leiolepis*), sedge (*Cyperus* spp.) (such as purple nutsedge (*Cyperus rotundus* L.), smallflower umbrella sedge (*Cyperus difformis* L.), yellow nutsedge (*Cyperus esculentus* L.) or amur *cyperus* (*Cyperus microiria* Steud.)); gramineae such as barnyardgrass (*Echinochloa crus-galli* L., *Echinochloa oryzicola* vasing.), crabgrass (*Digitaria* spp.) (such as summergrass (*Digitaria cili-* aris (Retz.) Koel), large crabgrass (*Digitaria sanguinalis* L.), violet crabgrass (*Digitaria violascens* Link) or *Digitaria horizontalis* Willd.), green foxtail (*Setaria viridis* (L.)), giant foxtail (*Setaria faberi* Herrm.), goosegrass (*Eleusine indica* L.), sorghum (*Sorghum* spp.) (such as johnsongrass (*Sorghum halepense* (L.) Pers.) or shattercane (*Sorghum bicolor* (L.) Moench.)), oat (*Avena* spp.) (such as wild oat (*Avena fatua* L.)), annual bluegrass (*Poa annua* L.), panic grass (*Panicum* spp.) (such as guinea grass (*Panicum maximum* Jacq.) or fall *panicum* (*Panicum dichotomiflorum* (L.) Michx.)), signal grass (*Brachiaria* spp.) (such as plantain signal grass (*Brachiaria plantaginea* (LINK) Hitchc.), palisade signal grass (*Brachiaria decumbens* Stapf) or mauritius signal grass (*Brachiaria mutica* (Forssk.) Stapf)), *paspalum* (*Paspalum* spp.), itchgrass (*Rottboellia cochinchinensis* (LOUR.) W. D. CLAYTON) or bermudagrass (*Cynodon dactylon* Pers.); scrophulariaceae such as persian speedwell (*Veronica persica* Poir.) or corn speedwell (*Veronica arvensis* L.); compositae such as beggar ticks (*Bidens* spp.) (such as hairy beggarticks (*Bidens pilosa* L.), devils berggarticks (*Bidens frondosa* L.), *Bidens biternata* (Lour.) Merr. et Sherff or beggarticks (*Bidens subalternans* DC.)), hairy fleabane (*Conyza bonariensis* (L.) Cronq.), horseweed (*Erigeron canadensis* L.), dandelion (*Taraxacum officinale* Weber), common cocklebur (*Xanthium strumarium* L.) or common ragweed (*Ambrosia artemisiifolia* L.); leguminosae such as rattlepod or rattlebox (*Crotalaria* spp.) (such as sunn-hemp (*Crotalaria juncea* L.)), poison bean (*Sesbania* spp.) (such as rostrate *sesbania* (*Sesbania rostrata* Bremek. & Oberm.) or *sesbania* pea (*Sesbania cannabina* (Retz.) Pers.)), white clover (*Trifolium repens* L.) or common *lespedeza* (*Lespedeza striata* (Thunb.) Hook. et. Arn.); caryophyllaceae such as sticky chickweed (*Cerastium glomeratum* Thuill.) or common chickweed (*Stellaria media* L.); euphorbiaceae such as garden spurge (*Euphorbia hirta* L.), threeseeded copperleaf (*Acalypha australis* L.) or fireplant (*Euphorbia heterophylla* L.); plantaginaceae such as asiatic plantain (*Plantago asiatica* L.); oxalidaceae such as creeping woodsorrel (*Oxalis corniculata* L.); apiaceae such as lawn pennywort (*Hydrocotyle sibthorpioides* Lam.); violaceae such as violet (*Viola mandshurica* W. Becker); iridaceae such as blue-eyedgrass (*Sisyrinchium rosulatum* Bicknell); geraniaceae such as carolina *geranium* (*Geranium carolinianum* L.); labiatae such as purple deadnettle (*Lamium purpureum* L.) or henbit (*Lamium amplexicaule* L.); malvaceae such as velvetleaf (*Abutilon theophrasti* MEDIC.) or prickly *sida* (*Sida spinosa* L.); convolvulaceae such as ivy-leaved morningglory (*Ipomoea hederacea* (L.) Jacq.), common morningglory (*Ipomoea purpurea* ROTH), cypressvine morningglory (*Ipomoea guamoclit* L.), *Ipomoea grandifolia* (DAMMERMANN) O'DONNELL, hairy *merremia* (*Merremia aegyptia* (L.) URBAN) or field bindweed (*Convolvulus arvensis* L.); chenopodiaceae such as common lambsquarters (*Chenopodium album* L.); portulacaceae such as common purslane (*Portulaca oleracea* L.); amaranthaceae such as pigweed (*Amaranthus* spp.) (such as prostrate pigweed (*Amaranthus blitoides* S. Wats.), livid amaranth (*Amaranthus lividus* L.), purple amaranth (*Amaranthus blitum* L.), smooth pigweed (*Amaranthus hybridus* L., *Amaranthus patulus* Bertol.), powell amaranth (*Amaranthus powellii* S. Wats.), slender amaranth (*Amaranthus viridis* L.), palmer amaranth (*Amaranthus palmeri* S. Wats.), redroot pigweed (*Amaranthus retroflexus* L.), tall waterhemp (*Amaranthus tuberculatus* (Moq.) Sauer.), common waterhemp (*Amaranthus tamariscinus* Nutt.), thorny amaranth (*Amaranthus spinosus* L.), ataco (*Amaranthus quitensis* Kunth.) or *Amaranthus rudis* Sauer.); solanaceae such as black nightshade (*Solanum nigrum* L.); polygonaceae such as spotted knotweed (*Polygonum lapathifolium* L.) or green smartweed (*Polygonum scabrum* MOENCH); cruciferae such as flexuous bittercress (*Cardamine flexuosa* WITH.); cucuribitaceae such as burcucumber (*Sicyos angulatus* L.); or commelinaceae such as common dayflower (*Commelina communis* L.).

The herbicidal composition of the present invention is very useful in practical application. For example, the herbicidal composition of the present invention has a remarkable synergistic effect, and has a favorable herbicidal activity even if the doses of the respective compounds A and B are small, and accordingly the impact on the surrounding environment can be suppressed.

Further, the herbicidal composition of the present invention is capable of controlling cyperaceae such as purple nutsedge (*Cyperus rotundus* L.) or yellow nutsedge (*Cyperus esculentus* L.); gramineae such as barnyardgrass (*Echinochloa crus-galli* L., *Echinochloa oryzicola* vasing.), summergrass (*Digitaria ciliaris* (Retz.) Koel), large crabgrass (*Digitaria sanguinalis* L.), shattercane (*Sorghum bicolor* (L.) Moench.), wild oat (*Avena fatua* L.), guinea grass (*Panicum maximum* Jacq.), signal grass (*Brachiaria* spp.) or bermudagrass (*Cynodon dactylon* Pers.); scrophulariaceae such as persian speedwell (*Veronica persica* Poir.); compositae such as hairy beggarticks (*Bidens pilosa* L.) or common ragweed (*Ambrosia artemisiifolia* L.); leguminosae such as sunnhemp (*Crotalaria juncea* L.), rostrate *sesbania* (*Sesbania rostrata* Bremek. & Oberm.) or common *lespedeza* (*Lespedeza striata* (Thunb.) Hook. et Am.); euphorbiaceae such as fireplant (*Euphorbia heterophylla* L.); malvaceae such as velvetleaf (*Abutilon theophrasti* MEDIC.); convolvulaceae such as ivy-leaved morningglory (*Ipomoea hederacea* (L.) Jacq.) or field bindweed (*Convolvulus arvensis* L.); or amaranthaceae such as redroot pigweed (*Amaranthus retroflexus* L.), which are problematic as noxious weeds in agricultural fields such as upland fields and orchards, and non-cropland such as golf courses, railway sides and roadsides, in a wide application timing including before and after the emergence. Further, it has a long lasting residual effect.

Further, since it comprises a combination of herbicides differing in the mode of action, it can control weeds having decreased sensitivity to many herbicides.

In consideration of the application site of the herbicidal composition or the type or growth state of the undesired plants, the herbicidal composition of the present invention may be mixed with or may be used in combination with other herbicides, fungicides, antibiotics, plant hormones, insecticides, fertilizers, phytotoxicity-reducing agents, etc., in addition to the above active ingredients, without departing from the intention and the scope of the present invention, whereby more excellent effects and activities may sometimes be obtained.

Such other herbicides may, for example, be (1) those which are believed to exhibit herbicidal effects by disturbing hormone activities of plants, (2) those which are believed to exhibit herbicidal effects by inhibiting photosynthesis of plants, (3) those which are believed to be converted to free radicals by themselves to form active oxygen in the plant body and show rapid herbicidal efficacy, (4) those which are believed to exhibit herbicidal effects by inhibiting chlorophyll biosynthesis of plants and abnormally accumulating a photosensitizing peroxide substance in the plant body, (5) those which are believed to exhibit herbicidal effects characterized by bleaching activities by inhibiting chromogenesis of plants such as carotenoids, (6) those which exhibit strong herbicidal effects specifically to gramineous plants, (7) those which are believed to exhibit herbicidal effects by inhibiting an amino acid biosynthesis of plants, (8) those which are believed to exhibit herbicidal effects by inhibiting cell mitoses of plants, (9) those which are believed to exhibit herbicidal effects by inhibiting protein biosynthesis or lipid biosynthesis of plants, and (10) those which are believed to exhibit herbicidal effects by being parasitic on plants.

The herbicidal composition of the present invention may be prepared by mixing compound A and compound B, as active ingredients, with various agricultural additives in accordance with conventional formulation methods for agricultural chemicals, and applied in various formulations such as dusts, granules, water dispersible granules, wettable powders, tablets, pills, capsules (including a formulation packaged by a water soluble film), water-based suspensions, oil-based suspensions, microemulsions, suspoemulsions, water soluble powders, emulsifiable concentrates, soluble concentrates or pastes. It may be formed into any formulation which is commonly used in this field, so long as the object of the present invention is thereby met.

At the time of the formulation, compound A and compound B may be mixed together for the formulation, or they may be separately formulated.

The additives to be used for the formulation include, for example, a solid carrier such as kaolinite, sericite, diatomaceous earth, slaked lime, calcium carbonate, talc, white carbon, kaoline, bentonite, clay, sodium carbonate, sodium bicarbonate, mirabilite, zeolite or starch; a solvent such as water, toluene, xylene, solvent naphtha, dioxane, dimethylsulfoxide, N,N-dimethylformamide, dimethylacetamide, N-methyl-2-pyrrolidone or an alcohol; an anionic surfactant such as a salt of fatty acid, a benzoate, a polycarboxylate, a salt of alkylsulfuric acid ester, an alkyl sulfate, an alkylaryl sulfate, an alkyl diglycol ether sulfate, a salt of alcohol sulfuric acid ester, an alkyl sulfonate, an alkylaryl sulfonate, an aryl sulfonate, a lignin sulfonate, an alkyldiphenylether disulfonate, a polystyrene sulfonate, a salt of alkylphosphoric acid ester, an alkylaryl phosphate, a styrylaryl phosphate, a salt of polyoxyethylene alkyl ether sulfuric acid ester, a polyoxyethylene alkylaryl ether sulfate, a salt of polyoxyethylene alkylaryl ether sulfuric acid ester, a polyoxyethylene alkyl ether phosphate, a salt of polyoxyethylene alkylaryl phosphoric acid ester, a salt of polyoxyethylene aryl ether phosphoric acid ester, a naphthalene sulfonic acid condensed with formaldehyde or a salt of alkylnaphthalene sulfonic acid condensed with formaldehyde; nonionic surfactant such as a sorbitan fatty acid ester, a glycerin fatty acid ester, a fatty acid polyglyceride, a fatty acid alcohol polyglycol ether, acetylene glycol, acetylene alcohol, an oxyalkylene block polymer, a polyoxyethylene alkyl ether, a polyoxyethylene alkylaryl ether, a polyoxyethylene styrylaryl ether, a polyoxyethylene glycol alkyl ether, polyethylene glycol, a polyoxyethylene fatty acid ester, a polyoxyethylene sorbitan fatty acid ester, a polyoxyethylene glycerin fatty acid ester, a polyoxyethylene hydrogenated castor oil or a polyoxypropylene fatty acid ester; and a vegetable oil or mineral oil such as olive oil, kapok oil, castor oil, palm oil, camellia oil, coconut oil, sesame oil, corn oil, rice bran oil, peanut oil, cottonseed oil, soybean oil, rapeseed oil, linseed oil, tung oil or liquid paraffins. These additives may suitably be selected for use alone or in combination as a mixture of two or more of them, so long as the object of the present invention is met. Further, additives other than the above-mentioned may be suitably selected for use among those known in this field. For example, various additives commonly used, such as a filler, a thickener, an anti-settling agent, an anti-freezing agent, a dispersion stabilizer, a safener, an anti-mold agent, a bubble agent, a disintegrator and a binder, may be used. The mix ratio by weight of the active ingredients to such various additives in the herbicidal composition of the present invention may be from 0.001:99.999 to 95:5, preferably from about 0.005:99.995 to about 90:10.

As a method of applying the herbicidal composition of the present invention, a proper method can be employed among various methods depending upon various conditions such as the application site, the type of the formulation, and the type and the growth stage of the undesired plants to be controlled, and for example, the following methods may be mentioned.

1. Compound A and Compound B are mixed and formulated together, and the formulation is applied as it is.

2. Compound A and Compound B are mixed and formulated together, and the formulation is diluted to a predetermined concentration with e.g. water, and as the case requires, a spreader (such as a surfactant, a vegetable oil or a mineral oil) is added for application.

3. Compound A and Compound B are separately formulated, and the formulations are applied as they are.

4. Compound A and compound B are separately formulated, and as the case requires, the formulations are diluted to predetermined concentrations with e.g. water, and as the case requires, a spreader (such as a surfactant, a vegetable oil or a mineral oil) is added, and the formulations are applied.

5. Compound A and compound B are separately formulated, and the formulations are mixed when diluted to a predetermined concentration with e.g. water, and as the case requires, a spreader (such as a surfactant, a vegetable oil or a mineral oil) is added for application.

Preferred embodiments of the present invention will be described below, but the present invention is by no means restricted thereto.

[1] A herbicidal composition comprising as active ingredients compound A and compound B.

[2] The herbicidal composition according to [1], wherein the mixing ratio of compound A to compound B is from 1:0.2 to 1:50 by the weight ratio.

[3] A method for controlling undesired plants or inhibiting their growth, which comprises applying a herbicidally effective amount of compound A and a herbicidally effective amount of compound B to the undesired plants or to a place where they grow.

[4] The method according to [3], wherein compound A is applied in an amount of from 10 to 100 g/ha, and compound B is applied in an amount of from 20 to 500 g/ha.

[5] The method according to [3] or [4], wherein the undesired plants are cyperaceae, gramineae, scrophulariaceae, compositae, leguminosae, euphorbiaceae, malvaceae, convolvulaceae or amaranthaceae.

[6] The method according to [5], wherein the undesired plants are gramineae, scrophulariaceae, compositae, leguminosae, malvaceae or convolvulaceae.

[7] The composition according to [1], wherein compound B is at least one member selected from the group consisting of imazapic, hexazinone and their salts.

[8] The composition according to [1], wherein compound B is at least one member selected from the group consisting of imazapic, mesotrione and their salts.

[9] The composition according to [1], wherein compound B is imazapic.

[10] The composition according to [1], which contains flazasulfuron and imazapic in a mixing ratio of from 1:1 to 1:15 by the weight ratio.

[11] The composition according to [1], wherein compound B is hexazinone.

[12] The composition according to [1], which contains flazasulfuron and hexazinone in a mixing ratio of from 1:2 to 1:30 by the weight ratio.

[13] The composition according to [1], wherein compound B is mesotrione.

[14] The composition according to [1], which contains flazasulfuron and mesotrione in a mixing ratio of from 1:1 to 1:20 by the weight ratio.

[15] The method according to [3], wherein flazasulfuron is applied in an amount of from 10 to 50 g/ha, and imazapic is applied in an amount of from 50 to 150 g/ha.

[16] The method according to [15], wherein the undesired plants which are to be controlled or of which growth is to be inhibited, are gramineae, scrophulariaceae, compositae, leguminosae, malvaceae or convolvulaceae.

[17] The method according to [16], wherein the undesired plants are summergrass (*Digitaria ciliaris* (Retz.) Koel), large crabgrass (*Digitaria sanguinalis* L.), wild oat (*Avena fatua* L.), persian speedwell (*Veronica persica* Poir.), common ragweed (*Ambrosia artemisiifolia* L.), common *lespedeza* (*Lespedeza striata* (Thunb.) Hook. et Am.), velvetleaf (*Abutilon theophrasti* MEDIC.) or field bindweed (*Convolvulus arvensis* L.).

[18] The method according to [3], wherein flazasulfuron is applied in an amount of from 10 to 50 g/ha, and hexazinone is applied in an amount of from 100 to 300 g/ha.

[19] The method according to [18], wherein the undesired plants are gramineae, scrophulariaceae, malvaceae or convolvulaceae.

[20] The method according to [19], wherein the undesired plants are barnyardgrass (*Echinochloa crus-galli* L., *Echinochloa orvzicola* vasing.), shattercane (*Sorghum bicolor* (L.) Moench.), persian speedwell (*Veronica persica* Poir.), velvetleaf (*Abutilon theophrasti* MEDIC.), ivy-leaved morningglory (*Ipomoea hederacea* (L.) Jacq.) or field bindweed (*Convolvulus arvensis* L.).

[21] The method according to [3], wherein flazasulfuron is applied in an amount of from 10 to 50 g/ha, and mesotrione is applied in an amount of from 50 to 200 g/ha.

[22] The method according to [21], wherein the undesired plants are gramineae, leguminosae or convolvulaceae.

[23] The method according to [22], wherein the undesired plants are wild oat (*Avena fatua* L.), guinea grass (*Panicum maximum* Jacq.), rostrate *sesbania* (*Sesbania rostrata* Bremek. & Oberm.) or field bindweed (*Convolvulus arvensis* L.).

[24] The composition according to [1], which contains flazasulfuron and mesotrione in a mixing ratio of from 1:3 to 1:20 by the weight ratio.

[25] The method according to [3], wherein flazasulfuron is applied in an amount of from 10 to 30 g/ha, and mesotrione is applied in an amount of from 90 to 200 g/ha.

EXAMPLES

Now, the present invention will be described in further detail with reference to Test Examples. However, the present invention is by no means restricted to such specific Test Examples.

In Test Examples, water dispersible granules containing flazasulfuron as an active ingredient (tradename: SHIBAGEN DF, manufactured by Ishihara Sangyo Kaisha, Ltd.) was used as flazasulfuron, a wettable powder containing imazapic (manufactured by Wako Pure Chemical Industries, Ltd.) prepared by a conventional method was used as imazapic, a wettable powder containing hexazinone (manufactured by Wako Pure Chemical Industries, Ltd.) prepared by a conventional method was used as hexazinone, and a flowable containing mesotrione as an active ingredient (tradename: Callisto, manufactured by Syngenta) was used as mesotrione.

Test Example 1

Upland field soil was put into a 1/160,000 ha pot, and seeds of summergrass (*Digitaria ciliaris* (Retz.) Koeler) were sown. On the next day, predetermined amounts of flazasulfuron and imazapic were diluted with water (in an amount corresponding to 300 L/ha), and applied for soil treatment by a small sprayer.

On the 14th day after treatment, the state of growth of the summergrass was visually observed to determine the growth inhibition rate in accordance with the following evaluation standard. The growth inhibition rate (%) (measured value) and the growth inhibition rate (%) (calculated value) calculated by the Colby's formula are shown in Table 1.

Growth inhibition rate (%)=0 (equivalent to the non-treated area) to 100 (complete kill)

TABLE 1

| Compound | Dose (g/ha) | Growth inhibition rate (%) of summergrass | |
|---|---|---|---|
| | | Measured value | Calculated value |
| Flazasulfuron | 10 | 15 | — |
| Imazapic | 150 | 50 | — |
| Flazasulfuron + Imazapic | 10 + 150 | 80 | 58 |

Test Example 2

Upland field soil was put into a 1/160,000 ha pot, and seeds of ivy-leaved morningglory (*Ipomoea hederacea* (L.) Jacq.) were sown. On the next day, predetermined amounts of flazasulfuron and hexazinone were diluted with water (in an amount corresponding to 300 L/ha), and applied for soil treatment by a small sprayer.

On the 22nd day after treatment, the state of growth of the ivy-leaved morningglory was visually observed to determine the growth inhibition rate. The growth inhibition rate (%) (measured value) and the growth inhibition rate (%) calculated in the same manner as in Test Example 1 are shown in Table 2.

TABLE 2

| Compound | Dose (g/ha) | Growth inhibition rate (%) of ivy-leaved morningglory | |
|---|---|---|---|
| | | Measured value | Calculated value |
| Flazasulfuron | 10 | 0 | — |
| | 30 | 0 | — |
| | 50 | 40 | — |
| Hexazinone | 100 | 0 | — |
| | 200 | 30 | — |
| | 300 | 40 | — |
| Flazasulfuron + Hexazinone | 10 + 300 | 85 | 40 |
| | 30 + 200 | 78 | 30 |
| | 50 + 100 | 70 | 40 |

Test Example 3

Upland field soil was put into a 1/160,000 ha pot, and seeds of wild oat (*Avena fatua* L.) were sown. On the next day, predetermined amounts of flazasulfuron, mesotrione and imazapic were diluted with water (in an amount corresponding to 300 L/ha), and applied for soil treatment by a small sprayer.

On the 22nd day after treatment, the state of growth of the wild oat was visually observed to determine the growth inhibition rate. The growth inhibition rate (%) (measured value) and the growth inhibition rate (%) calculated in the same manner as in Test Example 1 are shown in Table 3.

TABLE 3

| Compound | Dose (g/ha) | Growth inhibition rate (%) of wild oat | |
|---|---|---|---|
| | | Measured value | Calculated value |
| Flazasulfuron | 30 | 40 | — |
| | 50 | 0 | — |
| Mesotrione | 100 | 0 | — |
| | 200 | 0 | — |
| Imazapic | 50 | 40 | — |
| | 100 | 40 | — |
| | 150 | 60 | — |
| Flazasulfuron + Mesotrione | 30 + 50 | 75 | 40 |
| | 30 + 100 | 75 | 40 |
| | 30 + 200 | 80 | 40 |
| Flazasulfuron + Imazapic | 30 + 50 | 75 | 64 |
| | 30 + 100 | 85 | 64 |
| | 30 + 150 | 85 | 76 |

Test Example 4

Upland field soil was put into a 1/160,000 ha pot, and seeds of guinea grass (*Panicum maximum* Jacq.) were sown. On the next day, predetermined amounts of flazasulfuron and mesotrione were diluted with water (in an amount corresponding to 300 L/ha), and applied for soil treatment by a small sprayer.

On the 22nd day after treatment, the state of growth of the guinea grass was visually observed to determine the growth inhibition rate. The growth inhibition rate (%) (measured value) and the growth inhibition rate (%) calculated in the same manner as in Test Example 1 are shown in Table 4.

TABLE 4

| Compound | Dose (g/ha) | Growth inhibition rate (%) of guinea grass | |
|---|---|---|---|
| | | Measured value | Calculated value |
| Flazasulfuron | 10 | 0 | — |
| Mesotrione | 200 | 0 | — |
| Flazasulfuron + Mesotrione | 10 + 200 | 70 | 0 |

Test Example 5

Upland field soil was put into a 1/160,000 ha pot, and seeds of field bindweed (*Convolvulus arvensis* L.) were sown. On the next day, predetermined amounts of flazasulfuron and hexazinone were diluted with water (in an amount corresponding to 300 L/ha), and applied for soil treatment by a small sprayer.

On the 22nd day after treatment, the state of growth of the field bindweed was visually observed to determine the growth inhibition rate. The growth inhibition rate (%) (measured value) and the growth inhibition rate (%) calculated in the same manner as in Test Example 1 are shown in Table 5.

TABLE 5

| Compound | Dose (g/ha) | Growth inhibition rate (%) of field bindweed | |
|---|---|---|---|
| | | Measured value | Calculated value |
| Flazasulfuron | 30 | 0 | — |
| Hexazinone | 300 | 15 | — |
| Flazasulfuron + Hexazinone | 30 + 300 | 75 | 15 |

Test Example 6

Upland field soil was put into a 1/160,000 ha pot, and seeds of shattercane (*Sorghum bicolor* (L.) Moench.) were sown. On the next day, predetermined amounts of flazasulfuron and hexazinone were diluted with water (in an amount corresponding to 300 L/ha), and applied for soil treatment by a small sprayer.

On the 22nd day after treatment, the state of growth of the shattercane was visually observed to determine the growth inhibition rate. The growth inhibition rate (%) (measured value) and the growth inhibition rate (%) calculated in the same manner as in Test Example 1 are shown in Table 6.

TABLE 6

| Compound | Dose (g/ha) | Growth inhibition rate (%) of shattercane | |
|---|---|---|---|
| | | Measured value | Calculated value |
| Flazasulfuron | 30 | 60 | — |
| Hexazinone | 100 | 0 | — |
| Flazasulfuron + Hexazinone | 30 + 100 | 85 | 60 |

Test Example 7

Upland field soil was put into a 1/160,000 ha pot, and seeds of rostrate sesbania (*Sesbania rostrata* Bremek. & Oberm.) were sown. On the next day, predetermined amounts of flazasulfuron and mesotrione were diluted with water (in an amount corresponding to 300 L/ha), and applied for soil treatment by a small sprayer.

On the 22nd day after treatment, the state of growth of the rostrate *sesbania* was visually observed to determine the growth inhibition rate. The growth inhibition rate (%) (measured value) and the growth inhibition rate (%) calculated in the same manner as in Test Example 1 are shown in Table 7.

TABLE 7

| Compound | Dose (g/ha) | Growth inhibition rate (%) of rostrate sesbania | |
|---|---|---|---|
| | | Measured value | Calculated value |
| Flazasulfuron | 50 | 35 | — |
| Mesotrione | 50 | 15 | — |
| Flazasulfuron + Mesotrione | 50 + 50 | 60 | 45 |

Test Example 8

Upland field soil was put into a 1/160,000 ha pot, and seeds of persian speedwell (*Veronica persica* Poir.) were sown. On the next day, predetermined amounts of flazasulfuron and imazapic were diluted with water (in an amount corresponding to 300 L/ha), and applied for soil treatment by a small sprayer.

On the 21st day after treatment, the state of growth of the persian speedwell was visually observed to determine the growth inhibition rate. The growth inhibition rate (%) (measured value) and the growth inhibition rate (%) calculated in the same manner as in Test Example 1 are shown in Table 8.

TABLE 8

| Compound | Dose (g/ha) | Growth inhibition rate (%) of persian speedwell | |
| --- | --- | --- | --- |
| | | Measured value | Calculated value |
| Flazasulfuron | 50 | 20 | — |
| Imazapic | 50 | 50 | — |
| Flazasulfuron + Imazapic | 50 + 50 | 98 | 60 |

Test Example 9

Upland field soil was put into a 1/160,000 ha pot, and seeds of barnyardgrass (*Echinochloa crus-galli* L) were sown. On the next day, predetermined amounts of flazasulfuron and hexazinone were diluted with water (in an amount corresponding to 300 L/ha), and applied for soil treatment by a small sprayer.

On the 21st day after treatment, the state of growth of the barnyardgrass was visually observed to determine the growth inhibition rate. The growth inhibition rate (%) (measured value) and the growth inhibition rate (%) calculated in the same manner as in Test Example 1 are shown in Table 9.

TABLE 9

| Compound | Dose (g/ha) | Growth inhibition rate (%) of barnyardgrass | |
| --- | --- | --- | --- |
| | | Measured value | Calculated value |
| Flazasulfuron | 30 | 90 | — |
| Hexazinone | 100 | 0 | — |
| Flazasulfuron + Hexazinone | 30 + 100 | 98 | 90 |

Test Example 10

Upland field soil was put into a 1/160,000 ha pot, and seeds of persian speedwell (*Veronica persica* Poiret.) were sown. On the next day, predetermined amounts of flazasulfuron and hexazinone were diluted with water (in an amount corresponding to 300 L/ha), and applied for soil treatment by a small sprayer.

On the 21st day after treatment, the state of growth of the persian speedwell was visually observed to determine the growth inhibition rate. The growth inhibition rate (%) (measured value) and the growth inhibition rate (%) calculated in the same manner as in Test Example 1 are shown in Table 10.

TABLE 10

| Compound | Dose (g/ha) | Growth inhibition rate (%) of persian speedwell | |
| --- | --- | --- | --- |
| | | Measured value | Calculated value |
| Flazasulfuron | 30 | 15 | — |
| Hexazinone | 100 | 85 | — |
| Flazasulfuron + Hexazinone | 30 + 100 | 100 | 87 |

Test Example 11

Upland field soil was put into a 1/160,000 ha pot, and seeds of common ragweed (*Ambrosia artemisiifolia* L.) were sown. On the next day, predetermined amounts of flazasulfuron and imazapic were diluted with water (in an amount corresponding to 300 L/ha), and applied for soil treatment by a small sprayer.

On the 21st day after treatment, the state of growth of the common ragweed was visually observed to determine the growth inhibition rate. The growth inhibition rate (%) (measured value) and the growth inhibition rate (%) calculated in the same manner as in Test Example 1 are shown in Table 11.

TABLE 11

| Compound | Dose (g/ha) | Growth inhibition rate (%) of common ragweed | |
| --- | --- | --- | --- |
| | | Measured value | Calculated value |
| Flazasulfuron | 10 | 80 | — |
| Imazapic | 150 | 60 | — |
| Flazasulfuron + Imazapic | 10 + 150 | 98 | 92 |

Test Example 12

Upland field soil was put into a 1/160,000 ha pot, and seeds of common *lespedeza* (*Lespedeza striata* (Thunb.) Hook. et Arn.) were sown. On the next day, predetermined amounts of flazasulfuron and imazapic were diluted with water (in an amount corresponding to 300 L/ha), and applied for soil treatment by a small sprayer.

On the 21st day after treatment, the state of growth of the common *lespedeza* was visually observed to determine the growth inhibition rate. The growth inhibition rate (%) (measured value) and the growth inhibition rate (%) calculated in the same manner as in Test Example 1 are shown in Table 12.

TABLE 12

| Compound | Dose (g/ha) | Growth inhibition rate (%) of common lespedeza | |
| --- | --- | --- | --- |
| | | Measured value | Calculated value |
| Flazasulfuron | 30 | 90 | — |
| Imazapic | 50 | 0 | — |
| Flazasulfuron + Imazapic | 30 + 50 | 98 | 90 |

Test Example 13

Upland field soil was put into a 1/160,000 ha pot, and seeds of velvetleaf (*Abutilon theophrasti* MEDIC.) were sown. On the next day, predetermined amounts of flazasulfuron and imazapic were diluted with water (in an amount corresponding to 300 L/ha), and applied for soil treatment by a small sprayer.

On the 21st day after treatment, the state of growth of the velvetleaf was visually observed to determine the growth inhibition rate. The growth inhibition rate (%) (measured value) and the growth inhibition rate (%) calculated in the same manner as in Test Example 1 are shown in Table 13.

TABLE 13

| Compound | Dose (g/ha) | Growth inhibition rate (%) of velvetleaf | |
|---|---|---|---|
| | | Measured value | Calculated value |
| Flazasulfuron | 30 | 75 | — |
| Imazapic | 50 | 30 | — |
| Flazasulfuron + Imazapic | 30 + 50 | 93 | 83 |

Test Example 14

Upland field soil was put into a 1/160,000 ha pot, and seeds of velvetleaf (*Abutilon theophrasti* MEDIC.) were sown. On the next day, predetermined amounts of flazasulfuron and hexazinone were diluted with water (in an amount corresponding to 300 L/ha), and applied for soil treatment by a small sprayer.

On the 21st day after treatment, the state of growth of the velvetleaf was visually observed to determine the growth inhibition rate. The growth inhibition rate (%) (measured value) and the growth inhibition rate (%) calculated in the same manner as in Test Example 1 are shown in Table 14.

TABLE 14

| Compound | Dose (g/ha) | Growth inhibition rate (%) of velvetleaf | |
|---|---|---|---|
| | | Measured value | Calculated value |
| Flazasulfuron | 30 | 20 | — |
| Hexazinone | 200 | 30 | — |
| Flazasulfuron + Hexazinone | 30 + 200 | 80 | 44 |

Test Example 15

Upland field soil was put into a 1/160,000 ha pot, and seeds of field bindweed (*Convolvulus arvensis* L.) were sown. On the next day, predetermined amounts of flazasulfuron, mesotrione and imazapic were diluted with water (in an amount corresponding to 300 L/ha), and applied for soil treatment by a small sprayer.

On the 21st day after treatment, the state of growth of the field bindweed was visually observed to determine the growth inhibition rate. The growth inhibition rate (%) (measured value) and the growth inhibition rate (%) calculated in the same manner as in Test Example 1 are shown in Table 15.

TABLE 15

| Compound | Dose (g/ha) | Growth inhibition rate (%) of field bindweed | |
|---|---|---|---|
| | | Measured value | Calculated value |
| Flazasulfuron | 30 | 0 | — |
| Mesotrione | 200 | 60 | — |
| Imazapic | 150 | 15 | — |
| Flazasulfuron + Mesotrione | 30 + 200 | 75 | 60 |
| Flazasulfuron + Imazapic | 30 + 150 | 60 | 15 |

The entire disclosure of Japanese Patent Application No. 2013-033556 filed on Feb. 22, 2013 including specification, claims and summary is incorporated herein by reference in its entirety.

The invention claimed is:

1. A herbicidal composition comprising (A) flazasulfuron or its salt and (B) at least one herbicidal compound selected from the group consisting of imazapic, hexazinone, and their salts, wherein the weight ratio of (A) to (B) is from 1:0.2 to 1:50.

2. The composition according to claim 1, wherein the weight ratio of (A) to (B) is from 1:1 to 1:30.

3. The composition according to claim 2, wherein the weight ratio of (A) to (B) imazapic is from 1:1 to 1:15, and the weight ratio of (A) to (B) hexazinone is from 1:2 to 1:30.

4. The composition according to claim 3, wherein (A) is flazasulfuron, (B) is imazapic, and their weight ratio is from 1:1 to 1:15 by weight.

5. The composition according to claim 3, wherein (A) is flazasulfuron, (B) is hexazinone, and their weight ratio is from 1:2 to 1:30.

6. A method for controlling undesired plants or inhibiting their growth, which comprises applying a herbicidally effective amount of (A) flazasulfuron or its salt and a herbicidally effective amount of (B) at least one herbicidal compound selected from the group consisting of imazapic, hexazinone, and their salts, to the undesired plants or to a place where they grow, wherein (1) the weight ratio of (A) to (B) is from 1:0.2 to 1:50, and (2) the undesired plant is not a *Paspalum* species when (B) is imazapic or its salt.

7. The method according to claim 6, wherein (A) is applied in an amount of from 10 to 100 g/ha, and (B) is applied in an amount of from 20 to 500 g/ha.

8. The method according to claim 7, wherein (A) is applied in an amount of from 10 to 50 g/ha, and (B) is applied in an amount of from 50 to 300 g/ha.

9. The method according to claim 8, wherein (A) is applied in an amount of from 10 to 50 g/ha, and (B) at least one member selected from the group consisting of imazapic in an amount of from 50 to 150 g/ha and hexazinone in amount of from 100 to 300 g/ha is applied.

10. The method according to claim 9, wherein (A) is flazasulfuron and is applied in an amount of from 10 to 50 g/ha, and (B) is imazapic and is applied in an amount of from 50 to 150 g/ha.

11. The method according to claim 9, wherein (A) is flazasulfuron and is applied in an amount of from 10 to 50 g/ha, and (B) is hexazinone and is applied in an amount of from 100 to 300 g/ha.

12. The method according to claim 6, wherein the undesired plants are cyperaceae, gramineae, scrophulariaceae, compositae, leguminosae, euphorbiaceae, malvaceae, convolvulaceae or amaranthaceae.

13. The method according to claim 12, wherein the undesired plants are gramineae, scrophulariaceae, compositae, leguminosae, malvaceae or convolvulaceae.

14. The method according to claim 6, wherein (A) is flazasulfuron and is applied in an amount of from 10 to 50 g/ha, and (B) is imazapic and is applied in an amount of from 50 to 150 g/ha, to control undesired plants gramineae scrophulariaceae, compositae, leguminosae, malvaceae or convolvulaceae, or inhibit their growth.

15. The method according to claim 14, wherein the undesired plants are summergrass (*Digitaria ciliaris* (Retz.) Koel), large crabgrass (*Digitaria sanguinalis* L.), wild oat (*Avena fatua* L.), persian speedwell (*Veronica persica* Poir.), *Ambrosia artemisiifolia* L., common *lespedeza* (*Lespedeza striata* (Thunb.) Hook. et Arn.), velvetleaf (*Abutilon theophrasti* MEDIC.) or field bindweed (*Convolvulus arvensis* L.).

16. The method according to claim 6, wherein (A) is flazasulfuron and is applied in an amount of from 10 to 50 g/ha, and (B) is hexazinone and is applied in an amount of from 100 to 300 g/ha, to control undesired plants gramineae, scrophulariaceae, malvaceae or convolvulaceae, or inhibit their growth.

17. The method according to claim 16, wherein the undesired plants are barnyardgrass (*Echinochloa crus-galli* L., *Echinochloa oryzicola* vasing.), shattercane (*Sorghum bicolor* (L.) Moench.), persian speedwell (*Veronica persica* Poir.), velvetleaf (*Abutilon theophrasti* MEDIC.), ivy-leaved morningglory (*Ipomoea hederacea* (L.) Jacq.) or field bindweed (*Convolvulus arvensis* L.).

* * * * *